United States Patent [19]
Valle

[11] Patent Number: 4,969,903
[45] Date of Patent: Nov. 13, 1990

[54] HAIR IMPLANT SYSTEM

[76] Inventor: Wilfredo Valle, 141 W. 94th St., New York, N.Y. 10025

[21] Appl. No.: 435,669

[22] Filed: Nov. 13, 1989

[51] Int. Cl.$^5$ ............................................. A61F 2/10
[52] U.S. Cl. .................................................... 623/15
[58] Field of Search ............................. 623/15, 12, 66

[56] References Cited

U.S. PATENT DOCUMENTS

| | | | |
|---|---|---|---|
| 1,506,262 | 8/1924 | Slater | 128/339 |
| 3,003,155 | 10/1961 | Mielzynski et al. | 623/15 |
| 3,699,969 | 10/1972 | Allen | 623/15 |
| 4,458,678 | 7/1984 | Yannas et al. | 623/15 |

FOREIGN PATENT DOCUMENTS

| | | | |
|---|---|---|---|
| 2372621 | 8/1978 | France | 623/15 |
| 8808286 | 11/1988 | World Int. Prop. O. | 623/15 |

Primary Examiner—David J. Isabella

[57] ABSTRACT

The present disclosure relates to a method for implanting hair utilizing a hair implant system comprising a hair plug, a scalp perforator implement and an implant carrier implement. The method involves surgically preparing a scalp flap, perforating with a pyrimidically shaped needle to form a laterally extended perforation, passing the hair plug characterized by having a circular base and a central strand through the perforation so that the base anchors the plug under the flap and then suturing the flap in place.

2 Claims, 1 Drawing Sheet

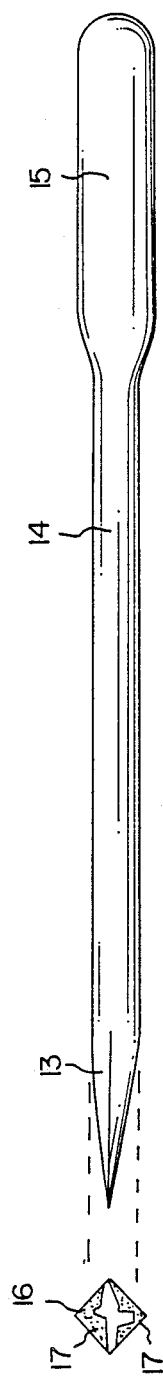
FIG. 2
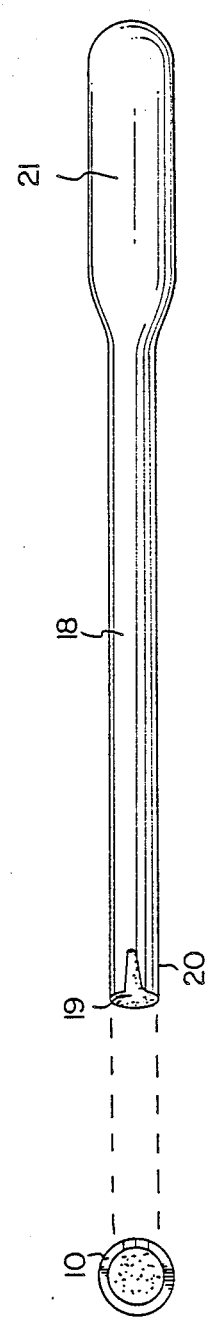
FIG. 3
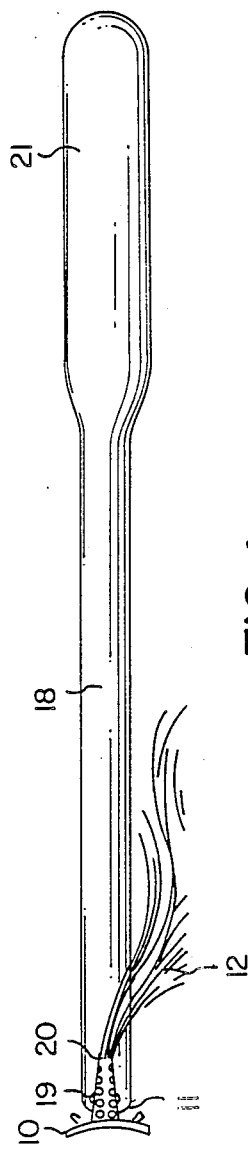
FIG. 4
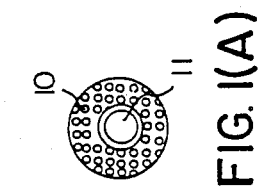
FIG. 1(A)
FIG. 1(B)
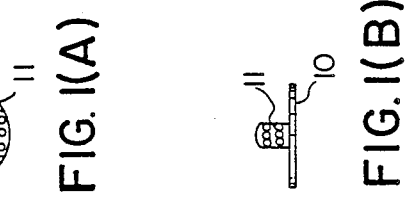
FIG. 1(C)

HAIR IMPLANT SYSTEM

BACKGROUND OF THE INVENTION

There are many procedures and materials now available to the bald or balding person to cover the bald areas of the scalp. These range from the simple covering of the area with a wig or toupee made of natural or synthetic hair to the Fusion process (gluing hair directly to the scalp) and hair weaving to procedures involving surgical intervention such as hair transplants, scalp reduction, the suture process or scalp flaps.

Each of these procedures suffers from serious deficiencies which limit the benefits they provide to the user. Such deficiencies can range from poor anchoring stability limiting the user in their freedom to engage in activities such as swimming or showering to the need to undergo numerous painful procedures with long healing periods and concomitant exposure to the risk of serious infection or rejection.

It would therefore be of great benefit to the people in need of permanent hair covering to have available a system that would provide a permanent hair implant that could be introduced in a single surgical procedure, that would have superior anchoring properties allowing the user full freedom of activity and would be easy to introduce by the cosmetic surgeon.

SUMMARY

The present invention relates to a novel hair transplant system that overcomes the many problems which has attended hair implant methods of the prior art. This systems comprises a hair plug, a scalp perforator implement and an implant carrier implement all of novel design and function.

DESCRIPTION OF THE DRAWING

The Drawing provides a top and side schematic view of the hair plug component of the present invention as well as side schematic views of the scalp perforating utensil, the implant carrier utensil and the implant carrier utensil in engaging relation with said hair plug.

DESCRIPTION OF THE PREFERRED EMBODIMENT

The present invention relates to a novel hair implant system consisting of a hair plug implant means, a scalp perforating utensil means and an implant carrier means. Use of such system allows ready implantation of synthetic or natural replacement hair into a bald scalp with only one surgical procedure thereby reducing trauma to the patient and decreasing the chances of rejection and infection. In addition the novel construction of the hair plug component allows ingrowth of tissue thus providing a strong anchor for the prothesis giving the patient full freedom of activity with the implanted hair. To better understand the hair implant system of the invention it will be described in detail with respect to the preferred embodiment shown in the Drawing.

FIG. 1(A) provides a top schematic view of a hair plug implant. It consists of a circular base 10 and a centrally disposed stem 11. The plug is made from a biologically inert material such as Dacron or Silicone. This is to reduce the possibility of inducing a rejection reaction in the recipient. In the preferred embodiment depicted the inert plastic is provided in the form of a thick, tightly woven mesh. The use of a mesh provides the means for allowing tissue to ingrow the plug after insertion. Suitable dimensions for the plug include a diameter of about 5 mm and a thickness of 0.5 mm for the base while the stem is a hollow cylinder in shape with a height of about 5 mm and a diameter of about 1.5 mm as more readily seen from the schematic side view provided in FIG. 1(B). FIG. 1(C) shows the hair plug in implant ready form. A plurality of natural or synthetic hair strands 12 are introduced into stem 11 and anchored to the base 10 using a strong surgical glue known in the art. The plug is sterilized before use employing methods that are compatible with the stability of natural or synthetic hair. Thus gas sterilization with ethylene oxide or radiation with gamma rays may be used. Excessive heat such as involved with steam sterilization should be avoided. Most preferably, each individual hair plug will carry about 40 hair strands.

FIG. 2 shows a side view of the scalp preforator utensil of the instant system. It is preferably a solid stainless steel needle having a pyrimidical shaped tip 13, a cylindrical stem 14 and a larger circumference handle end 15. Also depicted in FIG. 2 is a diagrammatical view of a scalp section 16 which has been perforated by the scalp perforator showing the four flaps 17 which are formed by this procedure. The scalp flaps facilitate the insertion of the hair plug implant through the scalp. Suitable dimensions for the scalp perforator are a length of about 18 cm and a diameter of about 2.5 mm for the stem.

FIG. 3 depicts a side view of an implant carrier utensil of the invention. At one end of the cylindrical stem 18 there is provided a hollow tip 19 and a side notch 20. The other end of the stem is formed into a larger circumference handle 21. The hollow tip end of the carrier utensil is constructed and arranged to engage and hold the hair plug stem thus allowing the surgeon to manipulate and insert the plug through the scalp perforation during the implant procedure. This engaged position of the carrier and the plug is shown in FIG. 4 with the plug ready to be implanted. Suitable dimensions for the carrier implement are a length of about 18 cm and a diameter of about 2.5 mm. The engaging notch at the hollow tip is about 7 mm long and about 2 mm wide. The carrier utensil, like the perforator implement, may be made of surgical grade stainless steel.

The surgical procedure by which the hair plug implants of the invention can be inserted can be briefly described as follows. The scalp is prepared in conventional manner for surgery using a conventional disinfectant. The area where the hair plug implants are to be used is outlined. Preferably a marking pencil or bonney's blue is used to make markings about 2.5 mm apart. After the area has been outlined, a forehead-lift incision is made extending behind the ear and back. Frontal and back flaps are raised.

With each flap being held upward, the surgeon utilizes the scalp perforator to make a perforation at each mark by inserting the implement inward through the scalp to produce the four flap configuration seen in FIG. 2. After each perforation is made in the scalp, the hair plug implant is inserted using the carrier to push the plug through the perforation flaps. The plug base is pushed through the scalp hole and the stem with its attached hair strands extends through the perforation. For best results it is suggested that the implants are started distal from the incision line working toward the incision line. After the implants are in place, the scalp is closed tightly, preferably using 3-0 clear nylon suture leaving a long end when the sutures are cut for ready access at the time of removal. As tissue growth occurs under the scalp the base will become ingrown with tissue and will be rigidly anchored in place under the scalp.

What is claimed is:

1. A method for implanting hair into a bald scalp said method comprising preparing scalp flaps surgically, inwardly perforating the scalp flaps with a pyrimidical shaped scalp perforating implement to produce a four flap configuration, inserting into each such perforation a hair plug implement comprising a circular base and a centrally located hollow cylindrical stem containing a plurality of anchored synthetic or natural hair strands whereby said base is inward of the scalp and the stem extends outward through said perforation and suturing the scalp flaps in place.

2. The method of claim 1 wherein said hair implant plug is made of tightly woven mesh thus allowing tissue to ingrow after implantation so as to anchor the implant.

* * * * *